United States Patent [19]

Thiele et al.

[11] 4,300,945
[45] Nov. 17, 1981

[54] SYNERGISTIC HERBICIDAL COMPOSITIONS

[75] Inventors: Gerald H. Thiele, Sunnyvale; Ashley H. Freiberg, Santa Clara; Robert L. Skiles; David L. King, both of Los Gatos, all of Calif.

[73] Assignee: Stauffer Chemical Company, Westport, Conn.

[21] Appl. No.: 118,933

[22] Filed: Feb. 6, 1980

Related U.S. Application Data

[63] Continuation-in-part of Ser. No. 27,224, Apr. 5, 1979, abandoned.

[51] Int. Cl.³ .................... A01N 43/36; A01N 41/00
[52] U.S. Cl. .......................... 71/95; 71/103; 71/111; 71/118
[58] Field of Search .................... 71/95, 103

[56] References Cited

U.S. PATENT DOCUMENTS

| | | | |
|---|---|---|---|
| 3,954,437 | 5/1976 | Gates et al. | 71/103 |
| 3,958,977 | 5/1976 | Prochaska et al. | 71/103 |
| 4,013,444 | 3/1977 | Fridinger | 71/103 |
| 4,110,105 | 8/1978 | Teach | 71/95 |
| 4,132,713 | 1/1979 | Broadhurst | 71/95 |
| 4,160,659 | 7/1979 | Rodebush et al. | 71/95 |

*Primary Examiner*—Glennon H. Hollrah
*Attorney, Agent, or Firm*—M. Henry Heines

[57] ABSTRACT

Synergistic herbicidal activity is displayed by compositions comprising the following two components:
(a) a pyrrolidone of the formula

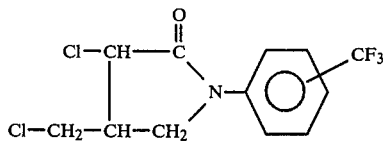

and
(b) an acetanilide of the formula

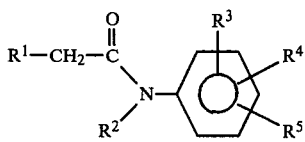

in which
$R^1$ is selected from the group consisting of hydrogen, $C_1$–$C_4$ alkyl, and chlorine;
$R^2$ is selected from the group consisting of hydrogen, $C_2$–$C_6$ alkoxyalkyl, and $C_3$–$C_6$ carbalkoxyalkyl;
$R^3$ is selected from the group consisting of hydrogen, $C_1$–$C_4$ alkyl, and chlorine;
$R^4$ is selected from the group consisting of hydrogen, $C_1$–$C_4$ alkyl, and chlorine; and
$R^5$ is selected from the group consisting of hydrogen, $C_1$–$C_4$ alkyl, chlorine, and —$NHSO_2CF_3$, at a weight ratio of (a) to (b) of from about 0.1:1 to about 50:1.

2 Claims, No Drawings

SYNERGISTIC HERBICIDAL COMPOSITIONS

CROSS REFERENCE TO RELATED APPLICATION

This is a continuation-in-part of application Ser. No. 027,224, filed Apr. 5, 1979, now abandoned.

BACKGROUND OF THE INVENTION

The protection of crops from weeds and other vegetation which inhibit crop growth by consuming valuable acreage or soil nutrients is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In many cases, active herbicides have been shown to be more effective in combination than when applied individually. The result is often termed "synergism", since the combination demonstrates a potency or activity level exceeding that which it would be expected to have, based on a knowledge of the individual potencies of the components. The present invention resides in the discovery that certain pyrrolidones and certain acetanilides, already known individually for their herbicidal potency, display this synergistic effect when applied in combination.

PRIOR ART

The two classes of compounds forming the combination which is the subject of the present invention are independently known in the art as active herbicides. Pyrrolidones are disclosed as herbicides in U.S. Pat. No. 4,110,105 (Teach, Aug. 29, 1979), and acetanilides are similarly disclosed in U.S. Pat. No. 3,442,945 (Olin, May 6, 1969), U.S. Pat. No. 3,780,090 (Akiba et al., Dec. 18, 1973), U.S. Pat. No. 3,816,092 (Wilson, June 11, 1974), U.S. Pat. No. 3,937,730 (Vogel et al., Feb. 10, 1976), and U.S. Pat. No. 3,894,078 (Fridinger, July 8, 1975).

DESCRIPTION OF THE INVENTION

It has now been discovered that synergism in the control of undesirable vegetation is exhibited by compositions comprising a mixture of the following two components:
(a) a pyrrolidone of the formula

| U.S. Pat. No. | Issue Date | Inventor | Assignee |
| --- | --- | --- | --- |
| 3,980,488 | 9/14/76 | Barrington et al | Sherwin-Williams |
| 2,378,786 | 6/19/45 | Osborne | Unassigned on Face |
| 2,637,711 | 5/5/53 | Aver | Unassigned on Face |

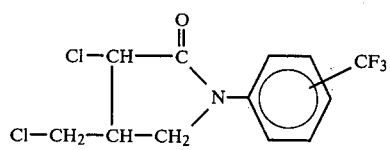

and
(b) an acetanilide of the formula

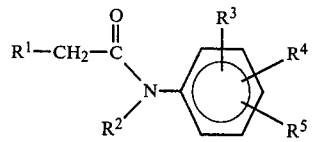

in which
$R^1$ is selected from the group consisting of hydrogen, $C_1-C_4$ alkyl, and chlorine;
$R^2$ is selected from the group consisting of hydrogen, $C_2-C_6$ alkoxyalkyl, and $C_3-C_6$ carbalkoxyalkyl;
$R^3$ is selected from the group consisting of hydrogen, $C_1-C_4$ alkyl, and chlorine;
$R^4$ is selected from the group consisting of hydrogen, $C_1-C_4$ alkyl, and chlorine; and
$R^5$ is selected from the group consisting of hydrogen, $C_1-C_4$ alkyl, chlorine, and $-NHSO_2CF_3$.

The terms "alkyl," "alkoxyalkyl," and "carbalkoxyalkyl" as used herein include both straight-chain and branched-chain alkyl groups. The term "alkoxyalkyl" refers to an alkyl group in which one hydrogen has been replaced by an alkoxy group. Examples are

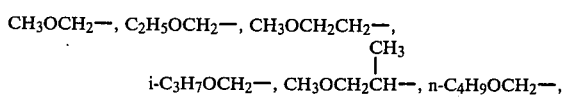

and $(CH_3)_2CHOCH_2-$. The term "carbalkoxyalkyl" refers to an alkyl group in which one hydrogen has been replaced by a carboxylic ester group at the carbonyl carbon. Examples are

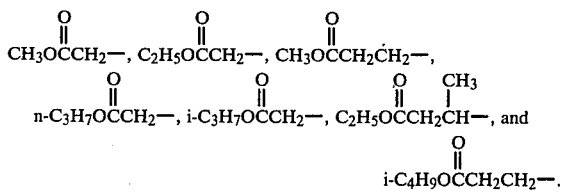

Examples of acetanilides useful in the present invention are:
2-chloro-N-methoxymethyl-2'-t-butyl-6'-methylacetanilide
2-chloro-N-butoxymethyl-2'-t-butyl-6'-methylacetanilide
2-chloro-N-methoxymethyl-2',6'-diethylacetanilide
2-chloro-N-methoxymethyl-2'-t-butyl-6'-ethylacetanilide
2-chloro-N-ethoxymethyl-2',6'-diethylacetanilide
2-chloro-N-isobutoxymethyl-2',6'-dimethylacetanilide
2-chloro-N-methoxymethyl-2'-t-butylacetanilide
2-chloro-N-isopropoxymethyl-2',6'-dimethylacetanilide
2-chloro-2'-t-butyl-6'-chloroacetanilide
2-chloro-2'-t-butyl-5'-methylacetanilide
3',4'-dichloropropionanilide
3',4'-dichloroisobutyranilide
3'-chloropropionanilide
2-chloro-N-(1-methoxy-prop-2-yl)-2'-ethyl-6'-methylacetanilide
2-chloro-N-carbethoxymethyl-2',6'-diethylacetanilide
3'-methylacetanilide 2',4'-dimethyl-5'-trifluoromethylsulfonylaminoacetanilide Of the acetanilides in the present composition, those of the following formula are preferred:

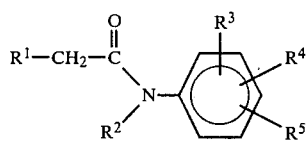

in which
R$^1$ is selected from the group consisting of hydrogen, methyl and chlorine;
R$^2$ is selected from the group consisting of hydrogen, C$_2$–C$_6$ alkoxyalkyl, and C$_3$–C$_6$ carbalkoxyalkyl;
R$^3$ is selected from the group consisting of methyl, ethyl, and chlorine;
R$^4$ is selected from the group consisting of methyl, ethyl, and chlorine; and
R$^5$ is selected from the group consisting of hydrogen and —NHSO$_2$CF$_3$.

All acetanilides within the scope of the invention can be prepared by the procedures described in the references listed above. The pyrrolidones can be prepared by procedures described in U.S. Pat. No. 4,110,105.

The terms "synergism" and "synergistic" are used herein to convey the result observed when a combination of herbicides demonstrates a potency in excess of that which the combination would be expected to produce on the basis of the potencies of each herbicide applied individually.

The term "herbicide" is used herein to denote a compound which controls or modifies the growth of plants. The term "herbicidally effective amount" is used to indicate the quantity of such a compound or combination of such compounds which is capable of producing a controlling or modifying effect. Controlling or modifying effects include all deviations from natural development, for example, killing, retardation, defoliation, desiccation, regulation, stunting, tillering, stimulating, leaf burn, dwarfing and the like. The term "plants" is used to include germinating seeds, emerging seedlings and established vegetation, including roots and aboveground portions.

In the compositions of this invention, the pyrrolidone:acetanilide weight ratio at which the herbicidal response is synergistic lies within the range of about 0.1:1 to about 50:1, preferably about 0.1:1 to about 20:1.

Application rates will depend upon the weeds to be controlled and the degree of control desired. In general, the compositions of this invention are most efficiently employed at a rate of 0.01 to 50 pounds per acre (0.011 to 56 kilograms per hectare) of the active ingredient, preferably 0.1 to 25 pounds per acre (0.11 to 28 kilograms per hectare).

The following examples provide further illustrations demonstrating the synergistic herbicidal response of the present compositions.

EXAMPLE I

This example demonstrates the synergistic response of 1-m-trifluoromethylphenyl-3-chloro-4-chloromethyl-2-pyrrolidone and 2',4'-dimethyl-5'-trifluoromethylsulfonylaminoacetanilide in combined postemergence application to a variety of weeds.

Fiber flats measuring 14.6×25.4×7.0 cm were filled to a depth of 5.0 cm with loamy sand soil, containing 50 parts per million (ppm) of the commercial fungicide cis-N[(trichloromethyl)thio]-4-cyclohexene-1,2-dicarboximide (Captan®) and 18-18-18 fertilizer (percentages of N-P$_2$O$_5$-K$_2$O on a weight basis). Several rows were impressed across the width of each flat and each row was seeded with a single weed species. The weed species included were wild oat (*Avena fatua*), nutsedge (*Cyperus* sp.), annual morning glory (*Ipomoea* sp.), shattercane (*Sorghum bicolor*), and annual ryegrass (*Lolium multiflorum*). Ample seeds were planted to give about 20 to 50 seedlings per row after emergence depending on the size of the plants. The flats were then placed in a greenhouse for three weeks, where they were watered regularly.

At the end of this period, the foliage on the emergent weeds was sprayed with aqueous solutions of the test compounds. The quantities sprayed were such that the amount of each test compound applied per flat corresponded to the desired application rate in pounds per acre. In control flats, the test compounds were applied alone at various application rates, whereas in the test flats, solutions containing both compounds were applied. Additional flats not treated at all were used as a standard for measuring the extent of weed control occurring in the treated flats.

Four weeks after treatment, the control and test flats were compared to the standard and each row was rated visually in terms of percent control ranging from 0% to 100%, with 0% representing the same degree of growth as the same row in the standard and 100% representing complete kill of all weeds in the row. All types of plant injury were taken into consideration.

The results of these tests are listed in Table I in the columns headed by the symbol "O" (indicating the "observed" results). These results are compared with the expected results, shown in the columns headed by the symbol "E", derived from the control data using Limpel's formula (Limpel et al., 1962, "Weed Control by Dimethylchloroterephthalate Alone and in Certain Combinations," *Proc. NEWCC.*, Vol. 16, pp 48-53):

$$E = X + Y - \frac{XY}{100}$$

where
X=observed percent injury when one of the herbicides is used alone,
and
Y=observed percent injury when the other herbicide is used alone.

An asterisk (*) is used to indicate the tests where the results show synergism, i.e., where the observed result exceeds the expected result. It is clear from the table that synergism was widely evident over the entire range of application rates tested.

TABLE I

FOLIAR SPRAY TEST RESULTS

Pyrrolidone: 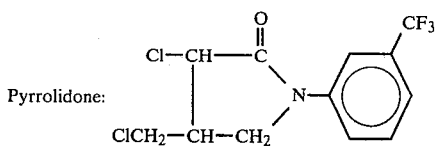

Acetanilide: 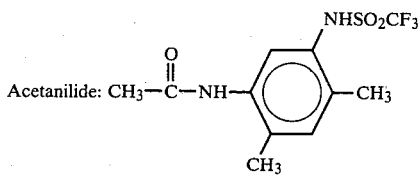

| Application Rates (lb/A) | | Percent Control - O: Observed E: Expected | | | | | | | | |
|---|---|---|---|---|---|---|---|---|---|---|
| | | Wild oat | | Nut-sedge | | Morning-glory | | Shatter-cane | | Ryegrass |
| Pyrroli-done | Acetani-lide | O | E | O | E | O | E | O | E | O | E |
| Control Data: | | | | | | | | | | | |
| 0.125 | — | 0 | | 0 | | 0 | | 0 | | 0 | |
| 0.25 | — | 0 | | 0 | | 0 | | 0 | | 0 | |
| 0.5 | — | 30 | | 10 | | 10 | | 20 | | 30 | |
| 1.0 | — | 60 | | 30 | | 20 | | 50 | | 50 | |
| — | 0.125 | 10 | | 65 | | 60 | | 65 | | 70 | |
| — | 0.25 | 20 | | 60 | | 60 | | 70 | | 75 | |
| — | 0.5 | 30 | | 40 | | 60 | | 75 | | 90 | |
| — | 1.0 | 80 | | 60 | | 60 | | 85 | | 95 | |
| Test Data: | | | | | | | | | | | |
| 0.125 | 0.125 | 0 | 10 | 50 | 65 | 60 | 60 | 65 | 65 | 20 | 70 |
| 0.125 | 0.25 | 30* | 20 | 60 | 60 | 60 | 60 | 70 | 70 | 70 | 75 |
| 0.125 | 0.5 | 85* | 30 | 70* | 40 | 60 | 60 | 85* | 75 | 95* | 90 |
| 0.125 | 1.0 | 100* | 80 | 75* | 60 | 60 | 60 | 95* | 85 | 100* | 95 |
| 0.25 | 0.125 | 85* | 10 | 70* | 65 | 60 | 60 | 80* | 65 | 80* | 70 |
| 0.25 | 0.25 | 85* | 20 | 70* | 60 | 60 | 60 | 85* | 70 | 85* | 75 |
| 0.25 | 0.5 | 90* | 30 | 70* | 40 | 60 | 60 | 90* | 75 | 95* | 90 |
| 0.25 | 1.0 | 95* | 80 | 75* | 60 | 60 | 60 | 95* | 85 | 100* | 95 |
| 0.5 | 0.125 | 40* | 37 | 75* | 69 | 50 | 64 | 85* | 72 | 60 | 79 |
| 0.5 | 0.25 | 90* | 44 | 90* | 64 | 50 | 64 | 90* | 76 | 85* | 83 |
| 0.5 | 0.5 | 100* | 51 | 90* | 46 | 60 | 64 | 95* | 80 | 90 | 93 |
| 0.5 | 1.0 | 100* | 86 | 90* | 64 | 75* | 64 | 98* | 88 | 90 | 97 |
| 1.0 | 0.125 | 100* | 64 | 85* | 76 | 90* | 68 | 95* | 83 | 100* | 85 |
| 1.0 | 0.25 | 100* | 68 | 85* | 72 | 90* | 68 | 90* | 85 | 100* | 88 |
| 1.0 | 0.5 | 100* | 72 | 85* | 58 | 75* | 68 | 95* | 88 | 100* | 95 |
| 1.0 | 1.0 | 100* | 92 | 85* | 72 | 70* | 68 | 98* | 93 | 100* | 98 |

*Synergistic effect shown.

EXAMPLE II

This example demonstrates the synergistic response of the same herbicides used in Example I on further weed species. Metal flats measuring 21.0×31.1×8.9 cm were used, and the weed species included wild oat as in Example I, plus downybrome (*Bromus tectorum*), Tartary buckwheat (*Fagopyrum tataricum*), and foxtail (*Setaria viridis*). The weed foliage was sprayed with the test solutions two weeks after the seeds were planted, and injury ratings were taken two weeks later.

The results are shown in Table II, with synergism highly evident.

TABLE II

FOLIAR SPRAY TEST RESULTS

Pyrrolidone: 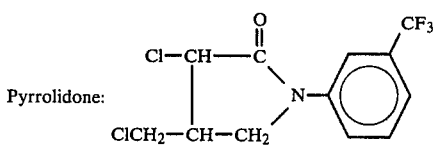

Acetanilide: 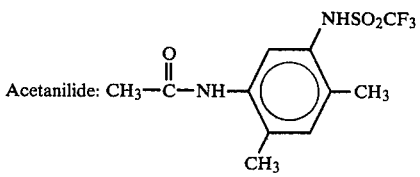

| Application Rates (lb/A) | | Percent Control - O: Observed E: Expected | | | | | | | |
|---|---|---|---|---|---|---|---|---|---|
| | | Downy brome | | Tartary Buck-wheat | | Wild Oat | | Foxtail | |
| Pyrroli-done | Acetani-lide | O | E | O | E | O | E | O | E |

| | Control Data: | | | | | | | | |
|---|---|---|---|---|---|---|---|---|---|
| 0.125 | — | 0 | | 0 | | 0 | | 0 | |
| 0.25 | — | 0 | | 0 | | 0 | | 0 | |
| 0.5 | — | 0 | | 0 | | 20 | | 40 | |
| — | 0.025 | 0 | | 0 | | 0 | | 0 | |
| — | 0.05 | 0 | | 0 | | 0 | | 0 | |
| — | 0.1 | 0 | | 0 | | 0 | | 0 | |
| | Test data: | | | | | | | | |
| 0.125 | 0.025 | 0 | 0 | 0 | 0 | 0 | 0 | 0 | 0 |
| 0.125 | 0.05 | 0 | 0 | 20* | 0 | 0 | 0 | 20* | 0 |
| 0.125 | 0.1 | 0 | 0 | 30* | 0 | 10* | 0 | 40* | 0 |
| 0.25 | 0.025 | 0 | 0 | 0 | 0 | 0 | 0 | 30* | 0 |
| 0.25 | 0.05 | 0 | 0 | 10* | 0 | 0 | 0 | 40* | 0 |
| 0.25 | 0.1 | 0 | 0 | 20* | 0 | 40* | 0 | 50* | 0 |
| 0.5 | 0.025 | 30* | 0 | 30* | 0 | 0 | 20 | 50* | 40 |
| 0.5 | 0.05 | 40* | 0 | 40* | 0 | 0 | 20 | 55* | 40 |
| 0.5 | 1.0 | 50* | 0 | 50* | 0 | 30* | 20 | 60* | 40 |

*Synergistic effect shown.

(Sesbania sp.), annual morning glory (Ipomoea sp.) and curly dock (Rumex crispus).

The tubs were then placed in a greenhouse and watered regularly. After three days, an additional row 1.25 cm deep was impressed in the soil, into which watergrass seeds (Echinochloa crusgalli) were placed. The soil was then pinched together over the row.

One week later, the soil was flooded with 5.0 cm of water containing appropriate quantities of test compounds to correspond to the desired application rates in pounds per acre. The water level was maintained over the next four weeks by adding water as needed. Injury ratings were then taken and the results are shown in Table III, where abundant synergism is shown.

TABLE III
FLOODED WEEDS TEST RESULTS

Pyrrolidone: 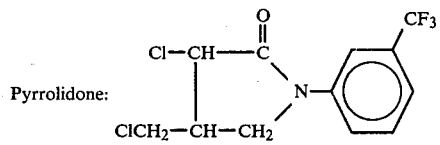

Acetanilide: 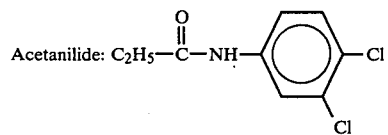

| Application Rates (lb/A) | | Percent Control - O: Observed E: Expected | | | | | | | | |
|---|---|---|---|---|---|---|---|---|---|---|
| | | Water-grass | | Nut-sedge | | Ses-bania | | Morning-glory | | Curly dock |
| Pyrroli-done | Acetani-lide | O | E | O | E | O | E | O | E | O | E |
| Control Data: | | | | | | | | | | |
| 0.125 | — | 20 | | 0 | | 0 | | 0 | | 95 | |
| 0.25 | — | 70 | | 0 | | 80 | | 10 | | 100 | |
| 0.5 | — | 100 | | 0 | | 90 | | 60 | | 100 | |
| — | 0.125 | 0 | | 0 | | 0 | | 0 | | 0 | |
| — | 0.25 | 0 | | 0 | | 95 | | 0 | | 100 | |
| — | 0.5 | 80 | | 0 | | 100 | | 100 | | 100 | |
| Test data: | | | | | | | | | | |
| 0.125 | 0.125 | 60* | 20 | 0 | 0 | 60* | 0 | 10* | 0 | 95 | 95 |
| 0.125 | 0.25 | 70* | 20 | 0 | 0 | 75 | 95 | 10* | 0 | | |
| 0.125 | 0.5 | 95* | 84 | 10* | 0 | | | | | | |
| 0.25 | 0.125 | 98* | 70 | 0 | 0 | 100* | 80 | 30* | 10 | | |
| 0.25 | 0.25 | 99* | 70 | 10* | 0 | | | 60* | 10 | | |
| 0.25 | 0.5 | 100* | 94 | 10* | 0 | | | | | | |
| 0.5 | 0.125 | | | 0 | 0 | 100* | 90 | 100* | 60 | | |
| 0.5 | 0.25 | | | 5* | 0 | | | 95* | 60 | | |
| 0.5 | 0.5 | | | 5* | 0 | | | | | | |

*Synergistic effect shown.
Blank spaces indicate 100% control in both observed and expected results, precluding evaluation of synergism.

EXAMPLE III

The herbicides used in this test were 1-m-trifluoromethylphenyl-3-chloro-4-chloromethyl-2-pyrrolidone and 3',4'-dichloropropionanilide. Unlike the tests in Examples I and II, this test was designed to measure synergistic activity in simulated flooded rice paddies.

Plastic tubs measuring 25.4×19.0×14.6 cm were filled to a depth of about 4.0 cm with sandy loam soil fortified with 200 ppm of Captan ® as a 50% wettable powder, and 50 ppm of 17-17-17 fertilizer. Several rows were impressed across the width of each flat and each row was seeded with a single plant species. Two rice species and four weed species were planted, the latter including yellow nutsedge (Cyperus esculentus), sesbania

EXAMPLE IV

In this example, simulated flooded rice paddies were used to test the herbicides 1-m-trifluoromethylphenyl-3-chloro-4-chloromethyl-2-pyrrolidone and 2-chloro-N-butoxymethyl-2',6'-diethylacetanilide. The same weed species and test procedure used in Example III were used here, except that the flooding was done six days after the watergrass seeds were planted, and injury ratings were taken nineteen days later.

The results are listed in Table IV. Again, substantial synergism is evident.

TABLE IV
Flooded Weeds Test Results

Pyrrolidone: 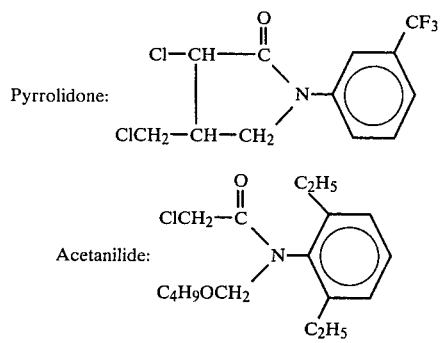

Acetanilide: 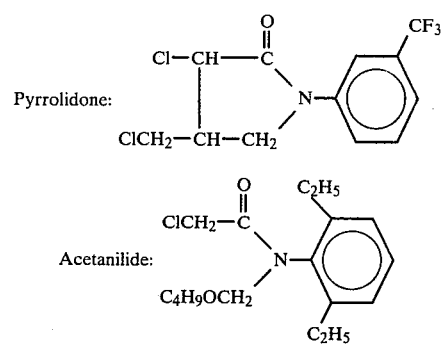

| Application Rates (lb/A) | | Percent Control - O: Observed E: Expected | | | | | | | | |
|---|---|---|---|---|---|---|---|---|---|---|
| | | Water-grass | | Nut-sedge | | Ses-bania | | Morning-glory | | Curly dock |
| Pyrroli-done | Acetani-lide | O | E | O | E | O | E | O | E | O | E |
| Control Data: | | | | | | | | | | | |
| 0.125 | — | 20 | | 0 | | 15 | | 0 | | 50 | |
| 0.25 | — | 70 | | 0 | | 30 | | 20 | | 60 | |
| 0.5 | — | 98 | | 0 | | 60 | | 50 | | 90 | |
| — | 0.0625 | 0 | | 0 | | 0 | | 0 | | 0 | |
| — | 0.125 | 0 | | 0 | | 0 | | 0 | | 0 | |
| Test data: | | | | | | | | | | | |
| 0.125 | 0.0625 | 60* | 20 | 0 | 0 | 20* | 15 | 10* | 0 | 40 | 50 |
| 0.125 | 0.125 | 60* | 20 | 0 | 0 | 20* | 15 | 20* | 0 | 60* | 50 |
| 0.25 | 0.0625 | 98* | 70 | 0 | 0 | 98* | 30 | 20 | 20 | 98* | 60 |
| 0.25 | 0.125 | 98* | 70 | 0 | 0 | 10 | 30 | 10 | 20 | 50 | 60 |
| 0.5 | 0.0625 | | | 0 | 0 | 100* | 60 | 60* | 50 | 100* | 90 |
| 0.5 | 0.125 | | | 0 | 0 | 100* | 60 | 50 | 50 | 100* | 90 |

*Synergistic effect shown.
Blank spaces indicate 100% control in both observed and expected results, precluding evaluation of synergism.

EXAMPLE V

Here again, flooded rice paddies were used according to the same procedure as described in Example III. The herbicides tested were 1-m-trifluoromethylphenyl-3-chloro-4-chloromethyl-2-pyrrolidone and 2-chloro-N-carbethoxymethyl-2′,6′-diethylacetanilide. The results are shown in Table V, demonstrating substantial evidence of synergism.

TABLE V
FLOODED WEEDS TEST RESULTS

Pyrrolidone: 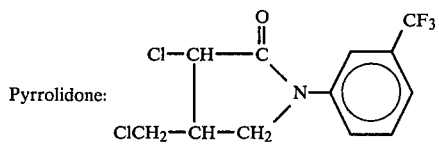

Acetanilide: 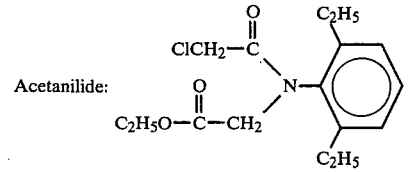

| Application Rates (lb/A) | | Percent Control - O: Observed E: Expected | | | | | | | | |
|---|---|---|---|---|---|---|---|---|---|---|
| | | Water-grass | | Nut-sedge | | Ses-bania | | Morning-glory | | Curly dock |
| Pyrroli-done | Acetani-lide | O | E | O | E | O | E | O | E | O | E |
| Control Data: | | | | | | | | | | | |
| 0.125 | — | 20 | | 0 | | 0 | | 0 | | 95 | |
| 0.25 | — | 70 | | 0 | | 80 | | 10 | | 100 | |
| 0.5 | — | 100 | | 0 | | 90 | | 60 | | 100 | |
| — | 0.125 | 90 | | 0 | | 0 | | 0 | | 0 | |
| — | 0.25 | 100 | | 30 | | 0 | | 0 | | 80 | |
| — | 0.5 | 100 | | 50 | | 0 | | 0 | | 100 | |
| Test data: | | | | | | | | | | | |
| 0.125 | 0.125 | 100* | 92 | 0 | 0 | 40* | 0 | 20* | 0 | 100* | 95 |
| 0.125 | 0.25 | | | 30 | 30 | 80* | 0 | 20* | 0 | | |
| 0.125 | 0.5 | | | 50 | 50 | 100* | 0 | 60* | 0 | | |
| 0.25 | 0.125 | | | 0 | 0 | 99* | 80 | 20* | 10 | | |
| 0.25 | 0.25 | | | ** | | 100* | 80 | 99* | 10 | | |
| 0.25 | 0.5 | | | 40 | 50 | 100* | 80 | 100* | 10 | | |

TABLE V-continued
FLOODED WEEDS TEST RESULTS

Pyrrolidone:
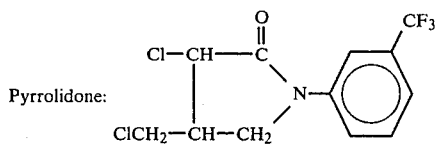

Acetanilide:
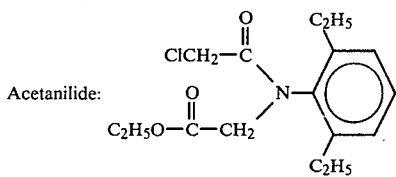

| Application Rates (lb/A) | | Percent Control - O: Observed E: Expected | | | | | | | | |
|---|---|---|---|---|---|---|---|---|---|---|
| | | Water-grass | | Nut-sedge | | Ses-bania | | Morning-glory | | Curly dock |
| Pyrroli-done | Acetani-lide | O | E | O | E | O | E | O | E | O E |
| 0.5 | 0.125 | | | 20* | 0 | 100* | 90 | 100* | 60 | |
| 0.5 | 0.25 | | | 10 | 30 | 100* | 90 | 100* | 60 | |
| 0.5 | 0.5 | | | 60* | 50 | 100* | 90 | 100* | 60 | |

*Synergistic effect shown.
**Test failed.
Blank spaces indicate 100% control in both observed and expected results, precluding evaluation of synergism.

EXAMPLE VI

The procedure of Example III on flooded rice paddies was used again, this time on the herbicides 1-m-trifluoromethylphenyl-3-chloro-4-chloromethyl-2-pyrrolidone and 2-chloro-N-(1-methoxy-prop-2-yl)-2'-ethyl-6'-methylacetanilide. The results are shown in Table VI, which offers substantial evidence of synergism.

TABLE VI
FLOODED WEEDS TEST RESULTS

Pyrrolidone:
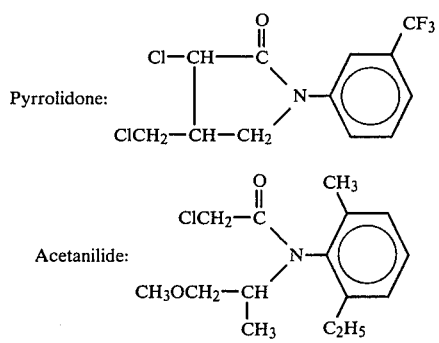

Acetanilide:
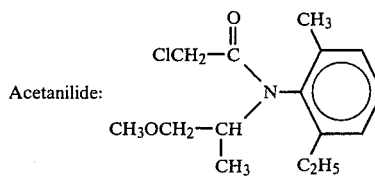

| Application Rates (lb/A) | | Percent Control - O: Observed E: Expected | | | | | | | | | |
|---|---|---|---|---|---|---|---|---|---|---|---|
| | | Water-grass | | Nut-sedge | | Ses-bania | | Morning-glory | | Curly dock | |
| Pyrroli-done | Acetani-lide | O | E | O | E | O | E | O | E | O | E |
| Control Data: | | | | | | | | | | | |
| 0.125 | — | 20 | | 0 | | 0 | | 0 | | 95 | |
| 0.25 | — | 70 | | 0 | | 80 | | 10 | | 100 | |
| 0.5 | — | 100 | | 0 | | 90 | | 60 | | 100 | |
| — | 0.125 | 75 | | 10 | | 0 | | 0 | | 0 | |
| — | 0.25 | 98 | | 0 | | 0 | | 0 | | 0 | |
| — | 0.5 | 100 | | 70 | | 0 | | 0 | | 100 | |
| Test data: | | | | | | | | | | | |
| 0.125 | 0.125 | 99* | 80 | 0 | 10 | 80* | 0 | 0 | 0 | 100* | 95 |
| 0.125 | 0.25 | | | 20* | 0 | 0 | 0 | 10* | 0 | 95 | 95 |
| 0.125 | 0.5 | | | 30 | 70 | 85* | 0 | 20* | 0 | | |
| 0.25 | 0.125 | 100* | 93 | 0 | 10 | 100* | 80 | 70* | 10 | | |
| 0.25 | 0.25 | | | 0 | 0 | 100* | 80 | 60* | 10 | | |
| 0.25 | 0.5 | | | 70 | 70 | 98* | 80 | 40* | 10 | | |
| 0.5 | 0.125 | | | 0 | 10 | 70 | 90 | 10 | 60 | | |
| 0.5 | 0.25 | | | 40* | 0 | 100* | 90 | 100* | 60 | | |

TABLE VI-continued
FLOODED WEEDS TEST RESULTS

Pyrrolidone: 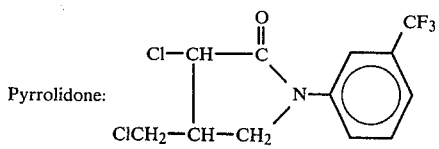

Acetanilide: 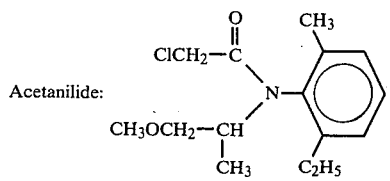

| Application Rates (lb/A) | | Percent Control - O: Observed E: Expected | | | | | | | | |
|---|---|---|---|---|---|---|---|---|---|---|
| | | Water-grass | | Nut-sedge | | Ses-bania | | Morning-glory | | Curly dock |
| Pyrroli-done | Acetani-lide | O | E | O | E | O | E | O | E | O | E |
| 0.5 | 0.5 | | | 60 | 70 | 100* | 90 | 100* | 60 | | |

*Synergistic effect shown.
Blank spaces indicate 100% control in both observed and expected results, precluding evaluation of synergism.

The compositions of this invention are useful as herbicides demonstrating synergistic activity for the control of undesirable vegetation. The compositions can be formulated in the same manner in which herbicides are generally formulated. The compounds may be applied either separately or combined as part of a two-part herbicidal system.

The object of the formulation is to apply the compositions to the locus where control is desired by a convenient method. The "locus" is intended to include soil, seeds, and seedlings, as well as established vegetation.

Formulations will generally contain several additives. Among these are some inert ingredients and diluent carriers such as organic solvents, water, oil and water, water in oil emulsions, carriers of dust and granules, and surface active, wetting, dispersing, and emulsifying agents.

Fertilizers, such as ammonium nitrate, urea and superphosphates may also be added.

Aids to rooting and growth, such as compost, manure, humus, sand, etc., may likewise be added.

The formulations are commonly dusts, wettable powders, granules, solutions or emulsifiable concentrates.

Dusts are free-flowing powder compositions containing the herbicidal compound impregnated on a particulate carrier. The particle size of the carrier is usually in the approximate range of 30 to 50 microns. Examples of suitable carriers are talc, bentonite, diatomaceous earth, and pyrophyllite. Anticaking and antistatic agents can be added, if desired. The composition generally contains up to 50% of active ingredient. Dusts, like liquid compositions can be applied from boom and hand or power sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols; salts of sulfonic acid; esters of long chain fatty acids; and polyhydric alcohols, in which the alcohol groups are free, omega-substituted polyethylene glycols of relatively long chain length.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

It is not necessary that the compositions be admixed with the soil particles. After application by the above discussed methods, they may be distributed below the soil surface to a depth of at least one-half inch by conventional means such as discing, dragging, or mixing.

What is claimed is:

1. A synergistic herbicidal composition consisting essentially of an effective amount of a mixture of (a) a pyrrolidone of the formula

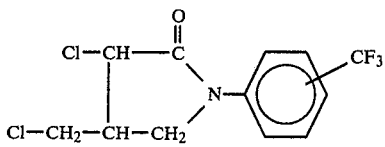

and (b) an acetanilide of the formula

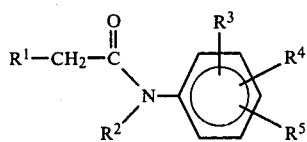

in which
R[1] is hydrogen;
R[2] is hydrogen;
R[3] is 2-methyl;
R[4] is 4-methyl; and
R[5] is 5—NHSO$_2$CF$_3$,
at a weight ratio of (a) to (b) of from about 0.125:1 to about 8:1.

2. A method of controlling undesirable vegetation which comprises applying to the locus where control is desired an effective amount of a herbicidal composition consisting essentially of a mixture of (a) a pyrrolidone of the formula

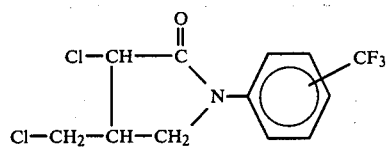

and
(b) an acetanilide of the formula

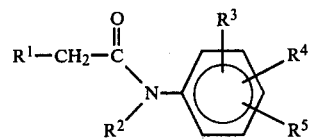

in which
R[1] is hydrogen;
R[2] is hydrogen;
R[3] is 2-methyl;
R[4] is 4-methyl; and
R[5] is 5—NHSO$_2$CF$_3$;
at a weight ratio of (a) to (b) of from about 0.125:1 to about 8:1.

* * * * *